(12) United States Patent
Nguyen et al.

(10) Patent No.: US 9,788,924 B2
(45) Date of Patent: *Oct. 17, 2017

(54) INTRAORAL DEVICE WITH BRIDGE

(71) Applicant: Incept, Inc., Fountain Valley, CA (US)

(72) Inventors: Thien Nguyen, Santa Ana, CA (US); Tam Thanh Pham, San Francisco, CA (US)

(73) Assignee: Dryshield, LLC, Fountain Valley, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/228,050

(22) Filed: Mar. 27, 2014

(65) Prior Publication Data

US 2014/0212838 A1   Jul. 31, 2014

Related U.S. Application Data

(63) Continuation of application No. 14/100,323, filed on Dec. 9, 2013, now Pat. No. 8,911,232.

(Continued)

(51) Int. Cl.
*A61C 17/06* (2006.01)
*A61C 17/02* (2006.01)

(52) U.S. Cl.
CPC .......... *A61C 17/04* (2013.01); *A61C 17/0208* (2013.01); *A61C 17/043* (2013.01)

(58) Field of Classification Search
CPC ..... A61C 17/043; A61C 17/046; A61C 17/04; A61C 17/0208

(Continued)

(56) References Cited

U.S. PATENT DOCUMENTS

| 50,461 | A | 10/1865 | Dibble |
| 1,471,207 | A | 10/1923 | Napoleon |

(Continued)

FOREIGN PATENT DOCUMENTS

| CA | 2851861 | 2/2016 |
| CN | 102026587 | 4/2011 |

(Continued)

OTHER PUBLICATIONS

U.S. Appl. No. 14/100,323; Final Office Action mailed Oct. 24, 2014.

(Continued)

*Primary Examiner* — Cris L Rodriguez
*Assistant Examiner* — Hao D Mai
(74) *Attorney, Agent, or Firm* — Polsinelli LLP

(57) ABSTRACT

A dental mouthpiece is provided that may be attached to a high-suction dental adapter for the purpose of assisting the dental staff during dental procedures through chair-side, hands-free suction, and isolation. Such mouthpiece may include a main body portion, a cheek retractor portion, and a suction connector portion. In some embodiments, the main body portion, cheek retractor portion, and suction connector portion (and sub-portions thereof) may be molded in one piece, preferably by injection molding. In an exemplary embodiment, the mouthpiece may be made of a material that is flexible, translucent, conducive to injection molding, high heat-resistant, and autoclavable. Such a material may include silicone. Because the mouthpiece may be made of a high heat-resistant and autoclavable material, such a mouthpiece may be reusable.

19 Claims, 11 Drawing Sheets

Related U.S. Application Data

(60) Provisional application No. 61/734,939, filed on Dec. 7, 2012.

(58) Field of Classification Search
USPC .............................................. 433/91–92, 140
See application file for complete search history.

(56) References Cited

U.S. PATENT DOCUMENTS

| | | | |
|---|---|---|---|
| 2,937,445 | A | 5/1960 | Erickson |
| 3,090,122 | A | 5/1963 | Erickson |
| 3,768,477 | A | 10/1973 | Anders et al. |
| 3,802,081 | A * | 4/1974 | Rogers ............. A61C 17/043 433/93 |
| 3,857,181 | A | 12/1974 | Rappaport |
| 3,877,691 | A | 4/1975 | Foster |
| 3,924,333 | A | 12/1975 | Erickson |
| 4,017,975 | A | 4/1977 | Johnson |
| 4,024,642 | A | 5/1977 | Zorovich |
| 4,083,115 | A * | 4/1978 | McKelvey ........... A61C 17/043 433/96 |
| 4,167,814 | A * | 9/1979 | Schubert ............. A61C 17/043 433/93 |
| 4,192,071 | A | 3/1980 | Erickson |
| 4,511,329 | A | 4/1985 | Diamond |
| 4,718,662 | A | 1/1988 | North |
| 4,802,851 | A | 2/1989 | Rhoades |
| 4,822,278 | A | 4/1989 | Oliva et al. |
| 5,037,298 | A | 8/1991 | Hickham |
| 5,078,602 | A | 1/1992 | Honoshofsky |
| 5,460,524 | A | 10/1995 | Anderson |
| 5,516,286 | A | 5/1996 | Kushner |
| 5,762,496 | A * | 6/1998 | Albertsson ........... A61C 17/043 433/93 |
| 5,890,899 | A | 4/1999 | Sclafani |
| 6,022,214 | A | 2/2000 | Hirsch et al. |
| 6,213,772 | B1 | 4/2001 | Costello |
| 6,267,591 | B1 | 7/2001 | Barstow |
| 6,338,627 | B2 | 1/2002 | Hirsch et al. |
| 6,575,746 | B2 | 6/2003 | Hirsch et al. |
| D495,799 | S | 9/2004 | Hirsch et al. |
| D497,426 | S | 10/2004 | Hirsch et al. |
| 6,908,308 | B2 | 6/2005 | Hirsch et al. |
| 6,974,321 | B2 | 12/2005 | Hirsch et al. |
| 7,287,981 | B2 | 10/2007 | Hirsch |
| 7,293,990 | B2 | 11/2007 | Hirsch et al. |
| 7,611,354 | B2 | 11/2009 | Hirsch et al. |
| D615,203 | S | 5/2010 | Hirsch et al. |
| 7,748,981 | B2 | 7/2010 | Hirsch et al. |
| 8,029,280 | B2 | 10/2011 | Black et al. |
| 8,057,227 | B2 | 11/2011 | Hirsch et al. |
| 8,057,228 | B2 | 11/2011 | Hirsch et al. |
| 8,075,310 | B2 | 12/2011 | Hirsch et al. |
| 8,297,973 | B2 | 10/2012 | Hirsch et al. |
| 8,529,256 | B2 | 9/2013 | Hirsch et al. |
| 8,535,056 | B2 | 9/2013 | Dragan et al. |
| D696,779 | S | 12/2013 | Hirsch et al. |
| 8,911,232 | B2 | 12/2014 | Nguyen |
| D734,851 | S | 7/2015 | Nguyen |
| 9,084,656 | B2 | 7/2015 | Hirsch |
| 9,089,389 | B2 | 7/2015 | Hirsch et al. |
| 9,358,086 | B2 | 6/2016 | Hirsch |
| 2003/0134253 | A1 | 7/2003 | Hirsch et al. |
| 2006/0063126 | A1 * | 3/2006 | Aloise .................. A61C 1/16 433/81 |
| 2006/0063129 | A1 | 3/2006 | Hirsch |
| 2006/0084031 | A1 | 4/2006 | Hirsch et al. |
| 2008/0166684 | A1 | 7/2008 | Kanas |
| 2008/0318183 | A1 | 12/2008 | Suzman |
| 2009/0123886 | A1 | 5/2009 | Vaska |
| 2009/0274991 | A1 | 11/2009 | Black et al. |
| 2011/0207076 | A1 | 8/2011 | Hirsch et al. |
| 2011/0311942 | A1 | 12/2011 | Black et al. |
| 2012/0015320 | A1 | 1/2012 | Koo |
| 2013/0095450 | A1 * | 4/2013 | Ames .................. A61C 17/043 433/93 |
| 2013/0252193 | A1 | 9/2013 | Bowman et al. |
| 2014/0004478 | A1 | 1/2014 | Hirsch et al. |
| 2014/0162209 | A1 | 6/2014 | Nguyen |
| 2014/0212837 | A1 | 7/2014 | Nguyen |
| 2014/0212839 | A1 | 7/2014 | Nguyen |
| 2014/0212840 | A1 | 7/2014 | Nguyen |
| 2014/0212841 | A1 | 7/2014 | Nguyen |
| 2015/0305842 | A1 | 10/2015 | Hirsch et al. |
| 2015/0335409 | A1 | 11/2015 | Hirsch |

FOREIGN PATENT DOCUMENTS

| | | |
|---|---|---|
| CN | 102247140 | 11/2011 |
| CN | 105578986 A | 5/2016 |
| EP | 2903557 | 8/2015 |
| GB | 2 170 106 | 7/1986 |
| WO | WO 99/37238 | 7/1999 |
| WO | WO 2015/088577 | 6/2015 |

OTHER PUBLICATIONS

PCT Application No. PCT/US2014/032892 International Search Report and Written Opinion dated Sep. 4, 2014.
Australian Patent Application No. 2014202637; AU Examination Report dated Jan. 23, 2015.
U.S. Appl. No. 29/491,367 Final Office Action mailed Mar. 4, 2015.
U.S. Appl. No. 29/491,367 Office Action mailed Nov. 14, 2014.
U.S. Appl. No. 29/477,887 Final Office Action mailed May 1, 2015.
U.S. Appl. No. 29/477,887 Office Action mailed Nov. 14, 2014.
U.S. Appl. No. 29/477,888 Final Office Action mailed May 1, 2015.
U.S. Appl. No. 29/477,888 Office Action mailed Nov. 14, 2014.
U.S. Appl. No. 14/100,323, Thien Nguyen, Intraoral Dental Suction and Isolation System, filed Dec. 9, 2013.
U.S. Appl. No. 14/228,046, Thien Nguyen, Intraoral Device With Mesh, filed Mar. 27, 2014.
U.S. Appl. No. 14/228,054, Thien Nguyen, Intraoral Device With Stability Start, filed Mar. 27, 2014.
U.S. Appl. No. 14/228,057, Thien Nguyen, Intraoral Device With Slit, filed Mar. 27, 2014.
U.S. Appl. No. 14/228,061, Thien Nguyen, Intraoral Device With Detachable Mouth Prop, filed Mar. 27, 2014.
U.S. Appl. No. 29/491,367, Thien Nguyen, Dental Mouthpiece, filed May 20, 2014.
U.S. Appl. No. 29/477,887, Thien Nguyen, Bridge Structure for Dental Mouthpiece, filed Dec. 27, 2013.
U.S. Appl. No. 29/477,888, Thien Nguyen, Cheek Retractor for Dental Mouthpiece, filed Dec. 27, 2013.
U.S. Appl. No. 14/228,046; Office Action mailed Nov. 6, 2015.
U.S. Appl. No. 14/228,054; Office Action mailed Dec. 3, 2015.
U.S. Appl. No. 14/228,057; Office Action mailed Nov. 20, 2015.
U.S. Appl. No. 14/228,061; Office Action mailed Dec. 4, 2015.
U.S. Appl. No. 29/477,887 Office Action mailed Nov. 127, 2015.
U.S. Appl. No. 29/477,888 Office Action mailed Dec. 2, 2015.
European Patent Application No. 14721736.8; Extended European Search Report dated Oct. 20, 2015.
U.S. Appl. No. 14/228,046; Final Office Action mailed Jun. 6, 2016.
U.S. Appl. No. 14/228,057; Final Office Action mailed Jun. 7, 2016.
U.S. Appl. No. 14/228,061; Final Office Action mailed Jun. 30, 2016.
U.S. Appl. No. 29/477,887 Final Office Action mailed Jun. 1, 2016.
U.S. Appl. No. 29/477,888 Final Office Action mailed Jun. 1, 2016.
Canadian Patent Application No. 2,919,142; CA Examination Report dated May 31, 2016.
U.S. Appl. No. 14/228,046; Office Action mailed Nov. 7, 2016.
U.S. Appl. No. 14/228,054; Final Office Action mailed Apr. 24, 2017.
U.S. Appl. No. 14/228,057; Office Action mailed Apr. 13, 2017.
U.S. Appl. No. 14/228,061; Office Action mailed Apr. 12, 2017.
Chinese Patent Application No. 201480039991.2 First Office Action dated Dec. 29, 2016.

(56) References Cited

OTHER PUBLICATIONS

U.S. Appl. No. 14/100,323; Office Action mailed May 6, 2014.

* cited by examiner

INTRAORAL DEVICE WITH BRIDGE

CROSS-REFERENCE TO RELATED APPLICATIONS

The present application is a continuation and claims the priority benefit of U.S. patent application Ser. No. 14/100,323 filed Dec. 9, 2013, which claims the priority benefit of U.S. provisional patent application No. 61/734,939 filed Dec. 7, 2012, the disclosure of which is incorporated herein by reference.

BACKGROUND OF THE INVENTION

1. Field of the Invention

The present invention generally relates to the field of dental mouthpieces. More specifically, the present invention relates to intraoral dental suction and isolation mouthpieces.

2. Description of Related Art

Various mouthpieces are currently used by dental health professionals, dental hygienists, and dental assistants in the field of dentistry. In the past, a dental patient has been treated by a traditional two-person team that comprises a dental professional and a dental assistant. Further, dental treatment may be provided by the team using many different types of dental equipment and materials. Such dental equipment and materials may include such items as an intraoral mirror, a bite block, a slow speed suction ejector, a high speed suction ejector, gauzes, cotton rolls, and dry angles. Each item of dental equipment may be used for different purposes, though some may be used in combination for some types of dental services. As such, a dental professional seeking to provide such dental services may need to use multiple items of such dental equipment. An important role of the dental assistant is therefore to assist the dental professional in coordinating the use of these multiple items of different equipment and materials.

There is, therefore, a need in the art for improved systems and methods of providing dental services in a more efficient, comfortable, and safe manner to the dental patient.

SUMMARY OF THE CLAIMED INVENTION

Embodiments of the present invention may include a mouthpiece that may be attached to a high-suction dental adapter for the purpose of assisting the dental staff during dental procedures through chair-side, hands-free suction, and isolation. Such a mouthpiece may comprise a main body portion, a cheek retractor portion, and a suction connector portion. In some embodiments, the main body portion, cheek retractor portion, and suction connector portion (and sub-portions thereof) may be molded in one piece, preferably by injection molding. In an exemplary embodiment, the mouthpiece may be made of a material that is flexible, translucent, conducive to injection molding, high heat-resistant, and autoclavable. Such a material may include silicone. Because the mouthpiece may be made of a high heat-resistant and autoclavable material, such a mouthpiece may be reusable.

The main body portion may comprise an enclosed pocket made up of an anterior wall, a posterior wall, and a side wall in between the anterior and posterior walls. The side wall may be perforated with a plurality of perforations. Such perforations may constitute a mesh. Additional perforations may be located on the anterior and posterior walls. The main body portion may further include a slit along a longitudinal, central axis on the anterior wall. Such openings (e.g., perforations and slit) allow for suction of air, fluids, and small debris from the patient's mouth, through the openings into the interior portion, and into the suction connector portion towards a suction source. Because the mouthpiece is made of a flexible and resilient material (e.g., silicone), the mouthpiece may be bent when placed in a patient's mouth to conform to the shape of the mouth. When properly positioned, the suction connector portion may protrude from one side of the patient's mouth, while the main body lies against the back of the patient's mouth, and the cheek retractor presses against the patient's cheek on the opposite side of the patient's mouth.

The main body may further include an protruding bridge structure on the interior surface of the posterior wall. Such a bridge structure may protrude from the interior surface in a wave shape with crests and troughs. The crests provide a plurality of contact points with the anterior wall to keep the anterior wall separated from the posterior wall during suction. Meanwhile, the troughs provide gaps that allow for suction of air, fluids, and small debris through the bridge structure.

DETAILED DESCRIPTION

Embodiments of the present invention provide for a mouthpiece comprising a main body portion, a cheek retractor portion, and a suction connector portion. In some embodiments, the main body portion, cheek retractor portion, and suction connector portion (and sub-portions thereof) may be molded as one-piece, preferably by injection molding. In an exemplary embodiment, the mouthpiece may be made of a material that is flexible, translucent, conducive to injection molding, high heat-resistant, and autoclavable. Such a material may include silicone. Because the mouthpiece may be made of a high heat-resistant and autoclavable material, such a mouthpiece may be reusable.

Figure 1A:
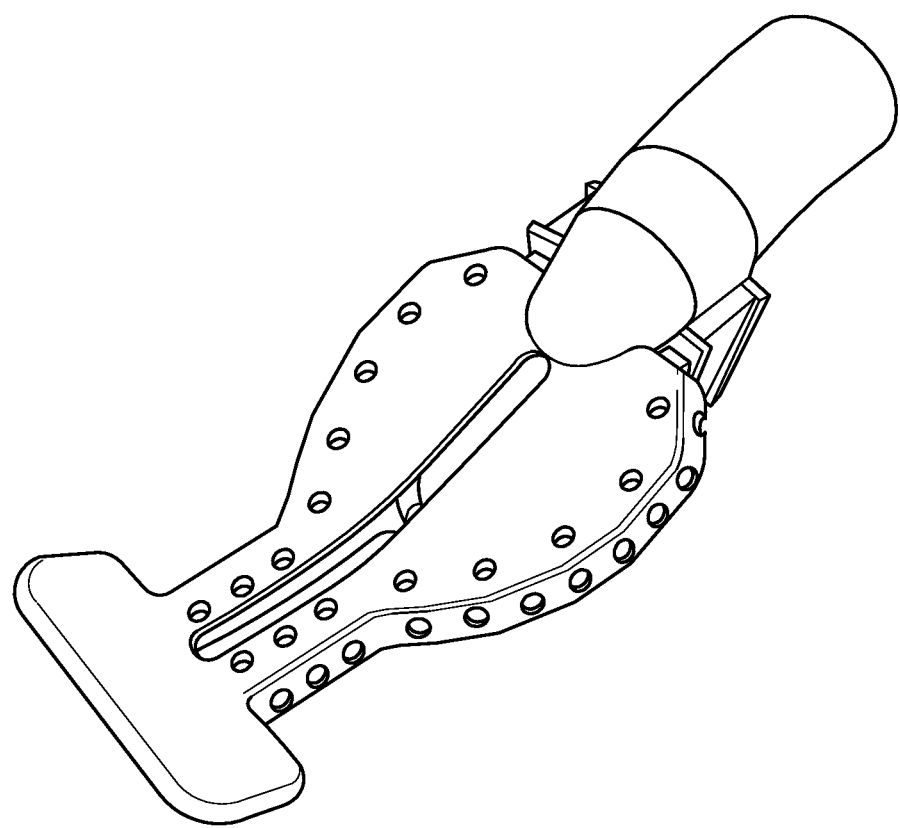
FIG. 1A is a perspective view of an exemplary mouthpiece with a detachable mouth prop.
Figure 1B:
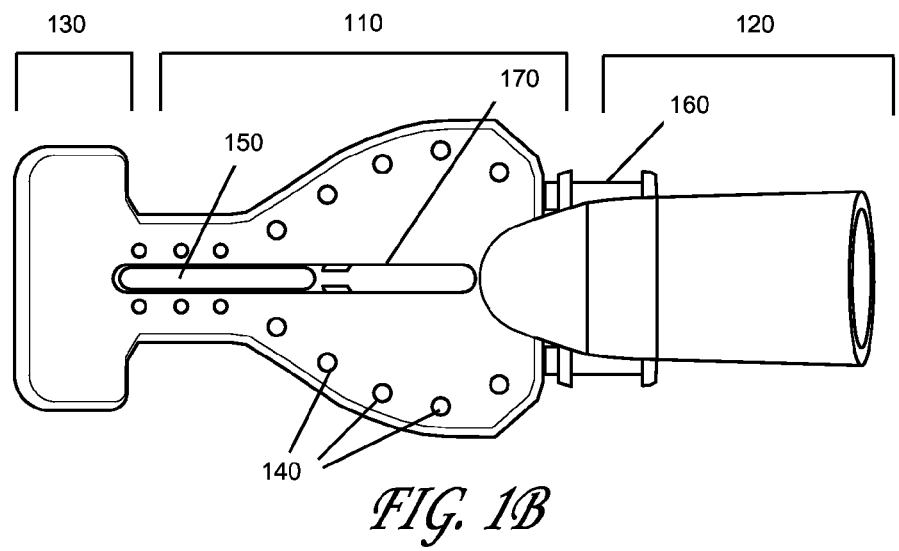
FIG. 1B is a top view of the exemplary mouthpiece and detachable mouth prop of FIG. 1A.
Figure 1C:
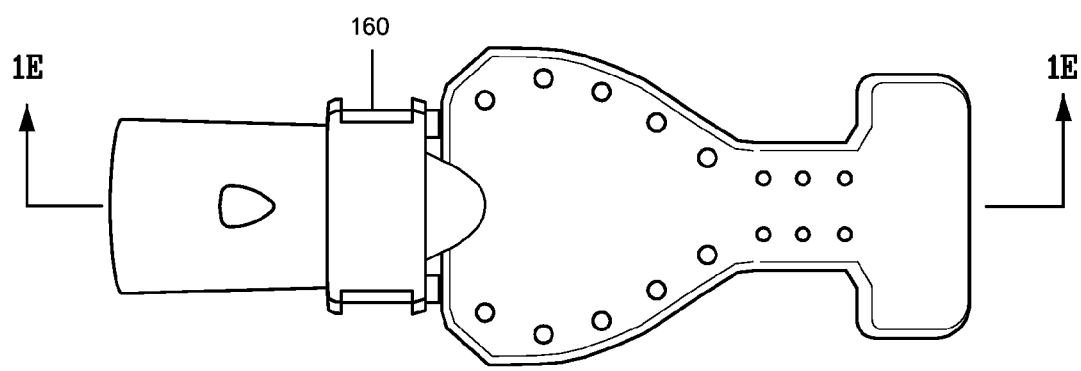
FIG. 1C is a bottom view of the exemplary mouthpiece and detachable mouth prop of FIG. 1A.
Figure 1D:
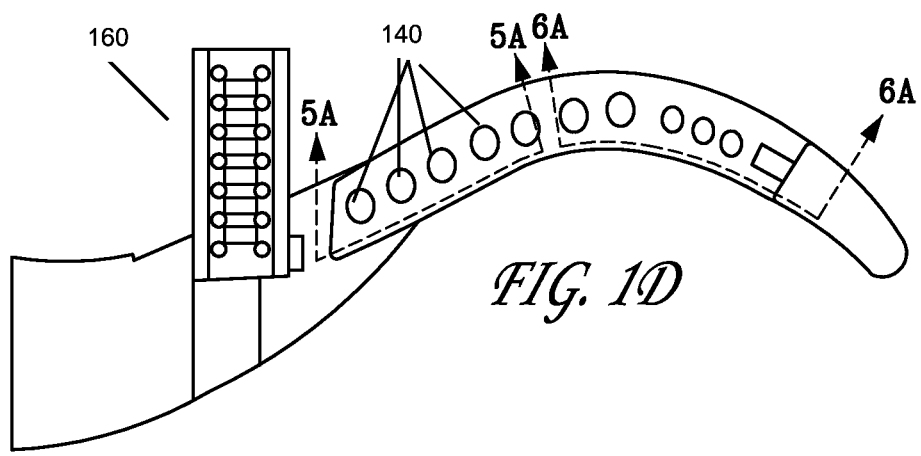
FIG. 1D is a side view of the exemplary mouthpiece and detachable mouth prop of FIG. 1A.

FIGS. 1A-E are different views of an exemplary mouthpiece with an attachable mouth prop 160, while FIGS. 2A-E are different views of the exemplary mouthpiece of FIG. 1A where the attachable mouth prop 160 has been detached. Such a mouthpiece may include a main body portion 110, a suction connector portion 120, and a cheek retractor portion 130.

The main body portion 110 may include mesh or perforations 140, a stability bar 150, an open slit 170, and an internal bridge 180. The main body potion 110 may connect to a suction connector portion 120 on one end and a cheek retractor portion 130 at the other end. Such a cheek retractor portion 130 may be configured to press against and retract a patient's cheek away from the patient's teeth. When placed in a patient's mouth, the suction connector portion 120 may protrude from one side of the patient's mouth, while the main body portion 110 lies against the back of the patient's mouth, and the cheek retractor portion 130 retracts the patient's cheek on the opposite side of the patient's mouth. The flexibility of the material used to form the mouthpiece allows for some bending when placed in the patient's mouth. The material is, however, resilient enough that the cheek retractor portion presses against the inside of the patient's cheek with such pressure being sufficient to move the cheek away from the patient's teeth.

An exemplary main body portion 110, when placed in a mouth, may include an anterior wall facing the front of the mouth (e.g., the side with slit 170) and a posterior wall facing the back of the mouth. The two walls may connect at a superior wall and an inferior wall forming a body that is at least partially enclosed.

Superior may be used herein to refer to the side that rests against a roof of a patient's mouth when placed therein, and inferior may be used to refer to the side that rests against the floor of the patient's mouth. The superior and inferior sides may be formed identically, which may allow for the mouthpiece to change orientation such that the superior side may appear as the inferior side and vice versa, in the new orientation. When in use, the respective sides of the main body portion 110 may serve to protect and separate the top of the mouth and the bottom of the mouth/tongue. In addition, the main body portion 110 may also serve to protect the back of the mouth (e.g., throat and airway) from falling debris.

Much of the main body portion 110 of the mouthpiece may be shaped as a straight-line arrowhead or shield whose base generally conforms to the intraoral shape of a patient's mouth. Differently-sized mouthpieces may be provided for differently-sized mouths of adults and children. Part of the base side of the arrowhead may be formed with thicker walls than the rest of the main body. Such thickening may provide additional stability.

Figure 4:
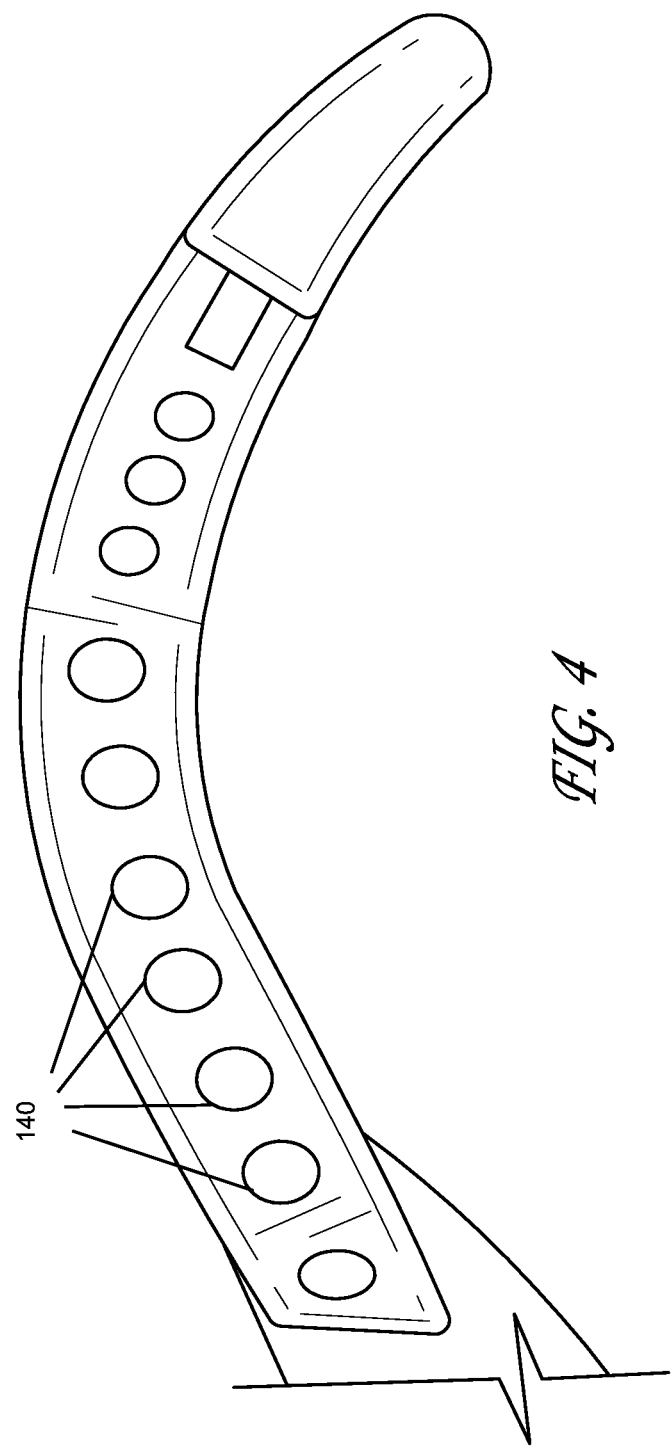
FIG. 4 is a close-up view of exemplary mesh sides in an exemplary mouthpiece.

In addition, the main body portion 110 of the mouthpiece may include a plurality of holes 140 distributed along the superior and inferior sides of the anterior and posterior walls to assist in suctioning of water, saliva and debris from the oral cavity. In some embodiments, a set of holes may also form a mesh along the walls of the superior and inferior edges. FIG. 4 is a close-up view of an exemplary mesh wall in an exemplary mouthpiece.

At the narrow end of the arrowhead that connects to the cheek retractor portion 130, the main body portion 110 may include a rectangular portion. Narrower than the base of the arrowhead, the rectangle may additionally include a reinforcing bar (or stability bar) 150 (described in further detail below) and may be at least partially crossed by a slit 170 (described in further detail below) into the interior of the pocket of the main body portion 110.

Figure 6A:
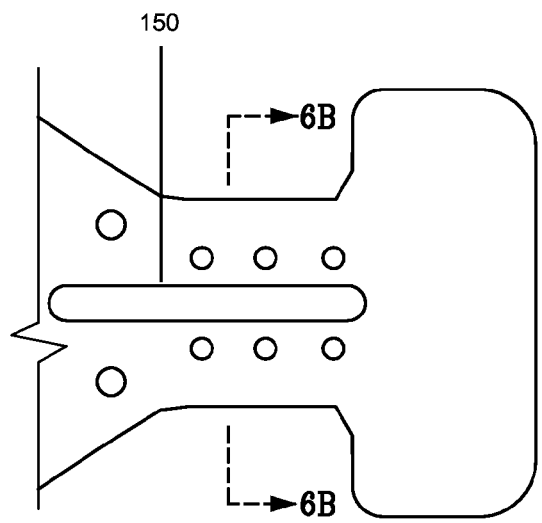
FIG. 6A is a close-up view of an exemplary reinforcing bar in an exemplary mouthpiece.
Figure 6B:
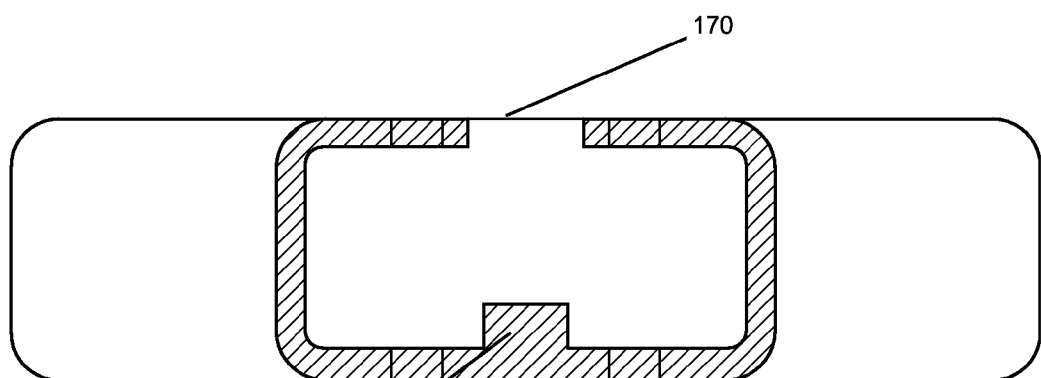
FIG. 6B is a cross-sectional view of the exemplary reinforcing bar of FIG. 6A.

Stability bar 150 may be a protrusion or otherwise a thickened area that reinforces the stability of the rectangular portion and assist in shaping this region to the intraoral posterior shape of a patient's mouth. FIG. 6A is a close-up view of an exemplary stability bar 150 of an exemplary mouthpiece. FIG. 6B is a cross-sectional view of the exemplary reinforcing bar in the cheek retractor connector portion of FIG. 6A.

In some embodiments, the internal, rectangular-shaped reinforcing or stability bar 150 may be located distally to the internal wavelike bridge structure 180 and attached to both the interior side of the posterior surface of the main body and the rectangular portion. Such a stability bar 150 may be located in the area where a positioned mouthpiece begins to wrap from the lingual side of the most posterior mandibular tooth, around the distal side of the most posterior tooth, and to anterior side of the most posterior mandibular tooth, thereby assisting in shaping the mouthpiece to the general intraoral shape of a patient's mouth.

Various embodiments of the mouthpiece may further include a longitudinal, open slit 170 extending over approximately two-thirds of the main body on the anterior surface. Running along the center of the main body across the rectangle and most of the arrowhead, such a slit 170 may assist in capture and suction of water, saliva and debris, as well as assisting in cleaning and maintenance.

Figure 1E:
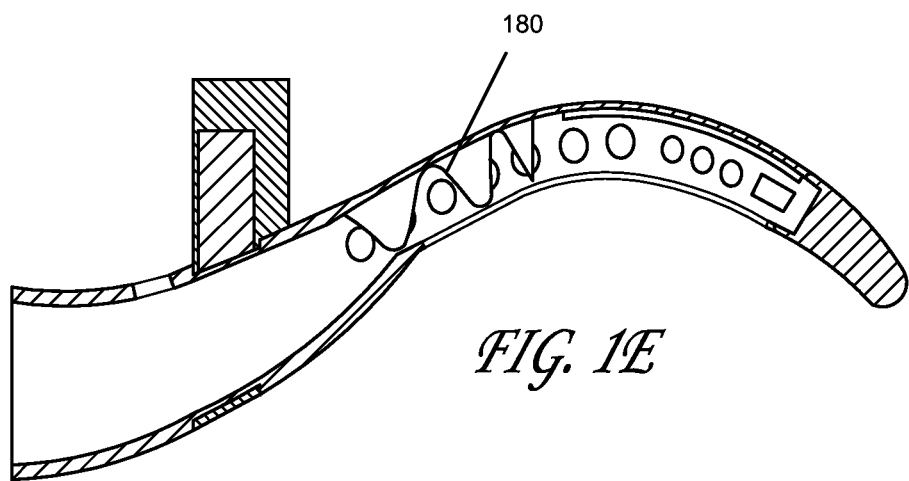
FIG. 1E is a cross-sectional view of the exemplary mouthpiece and detachable mouth prop of FIG. 1A.
Figure 2A:
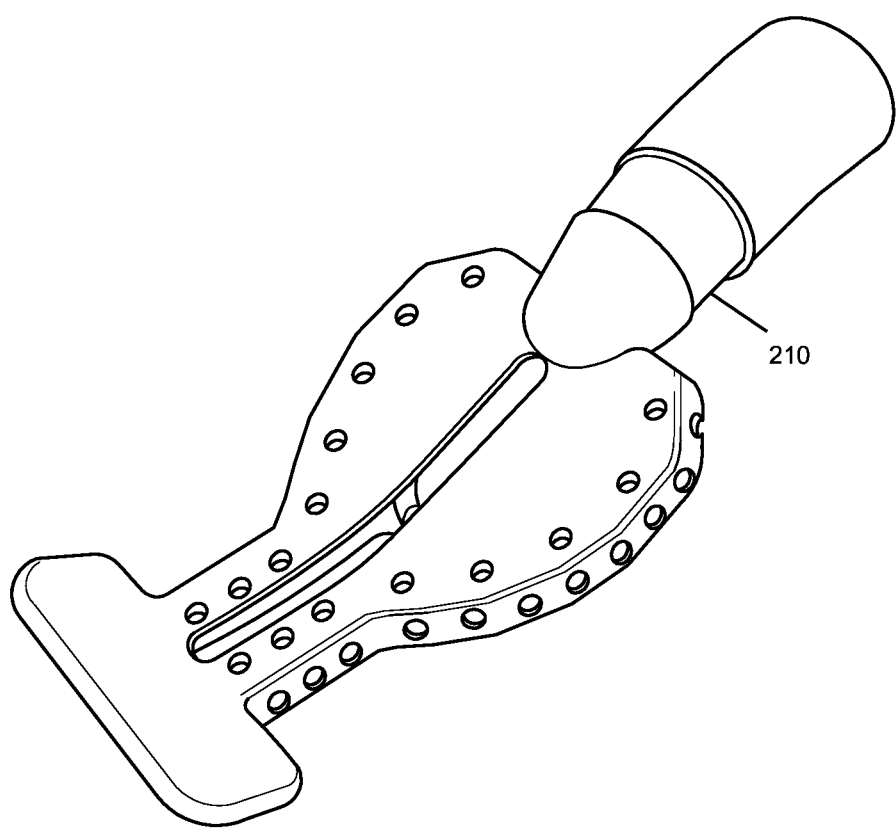
FIG. 2A is a perspective view of the exemplary mouthpiece of FIG. 1A where the detachable mouth prop has been detached.
Figure 2B:
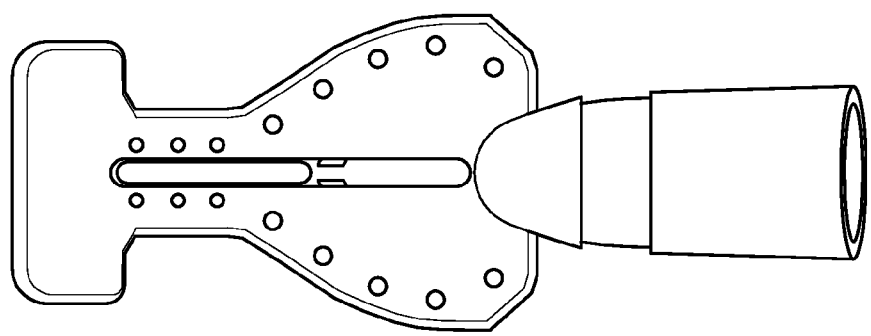
FIG. 2B is a top view of the exemplary mouthpiece of FIG. 2A.
Figure 2C:
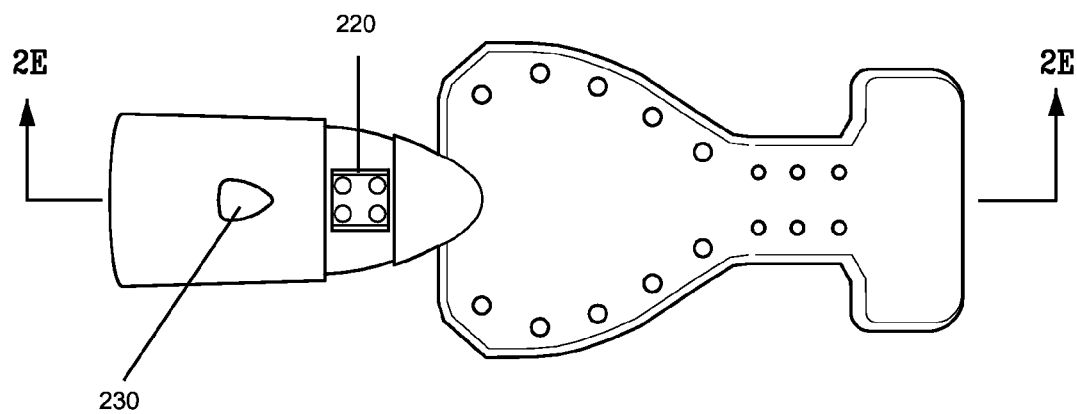
FIG. 2C is a bottom view of the exemplary mouthpiece of FIG. 2A.
Figure 2D:
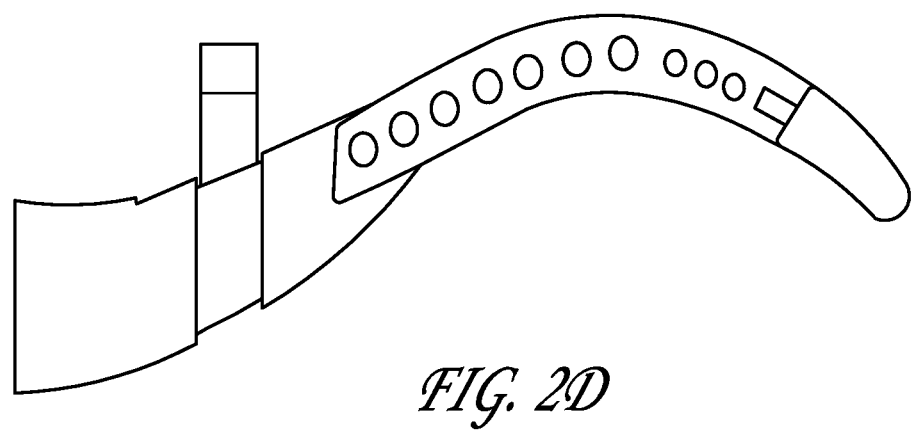
FIG. 2D is a side view of the exemplary mouthpiece of FIG. 2A.
Figure 2E:
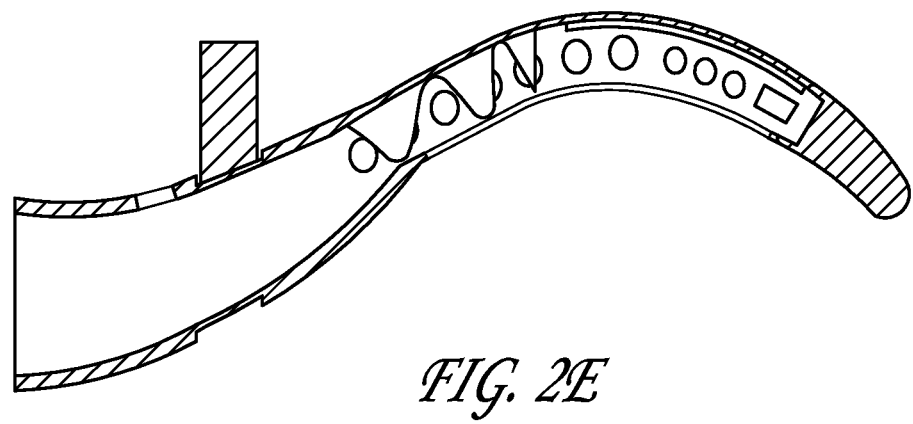
FIG. 2E is a cross-sectional view of the exemplary mouthpiece of FIG. 2A.
Figure 3A:
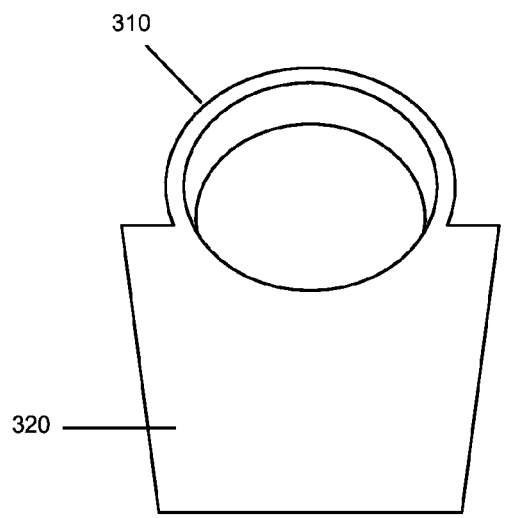
FIG. 3A is a front view of an exemplary mouth prop.
Figure 3D:
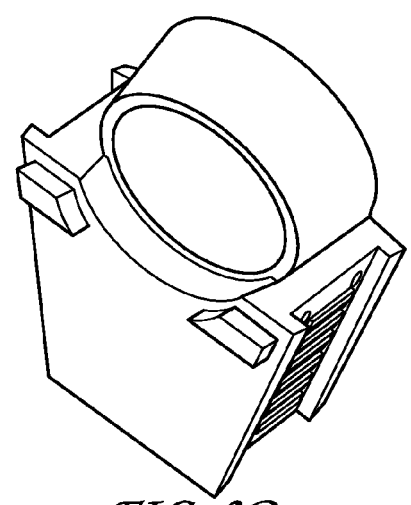
FIG. 3D is a perspective view of the exemplary mouth prop of FIG. 3A.
Figure 3B:
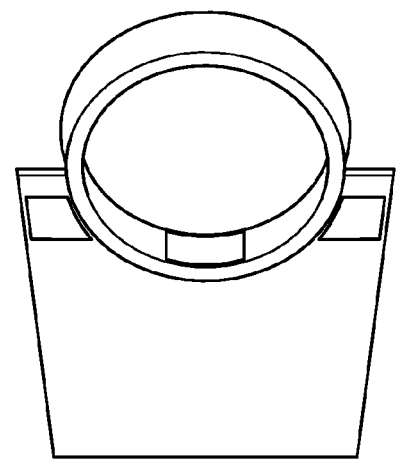
FIG. 3B is a back view of the exemplary mouth prop of FIG. 3A.
Figure 3E:
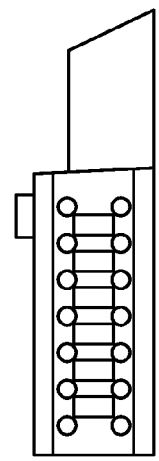
FIG. 3E is a side view of the exemplary mouth prop of FIG. 3A.
Figure 3C:
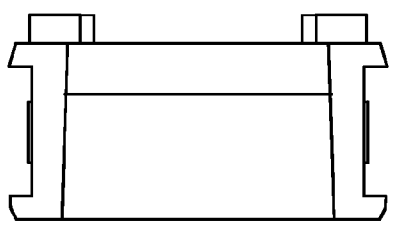
FIG. 3C is a bottom view of the exemplary mouth prop of FIG. 3A.
Figure 3F:
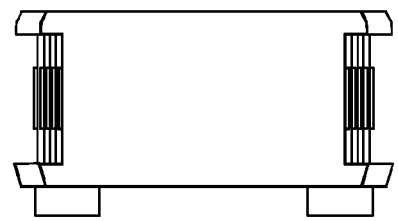
FIG. 3F is a top view of the exemplary mouth prop of FIG. 3A.
Figure 5:
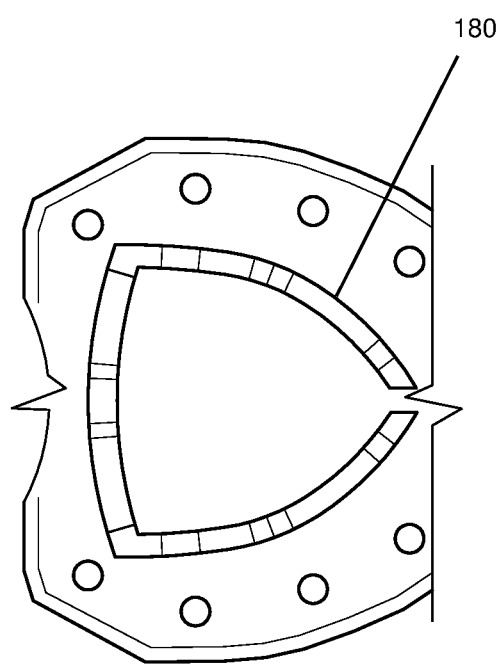
FIG. 5 is a close-up view of an internal bridge in an exemplary mouthpiece.

Additionally, the main body of the mouthpiece may include a bridge structure 180 on an interior surface to ensure that the anterior and posterior surfaces remain separated during suction. FIG. 1E is a cross-sectional view of the mouthpiece in which the bridge structure 180 is illustrated. FIG. 5 is a close-up view of the bridge structure 180 without the surrounding walls of the main body portion. Such a bridge structure 180 may be formed as an wave-like protrusion that generally corresponds to the distance between the anterior and posterior walls extending substantially (e.g., within 1 mm) the full distance at its crest and substantially flush to the surface at its trough. In some embodiments, the bridge structure 180 may be centrally-located in the main body portion 110 of the mouthpiece. The gaps (or troughs) between the waves of the bridge structure 180 assist in the suction-driven transfer of water and saliva to the suction connector portion 120 and ultimately, into a central suction vacuum. In some embodiments, the bridge structure 180 may follow the shape of a logo (e.g., an arrowhead or shield).

The suction connector portion 120 may be oval-shaped and also attached to the main body portion 110. The suction connector portion 120 may be formed with thicker walls than the main body portion 110 and configured to attach to a high-suction vacuum adapter and to assist in transferring water, saliva, and debris from the oral cavity to the external adapter for removal. The suction connector portion 120 may also include an internal stop to assist in sliding the mouthpiece onto the adapter to a desired depth. The suction connector portion 120 may additionally have an external, concave, notched region 210 that corresponds to a removable strap such that when the strap is in place, the external walls of the strap and the rest of the connector portion may be flush.

Figure 7A:
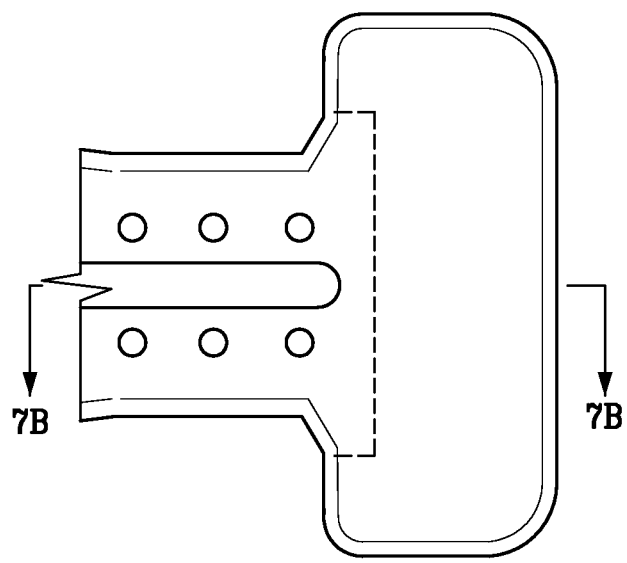
FIG. 7A is a close-up view of an exemplary cheek retractor portion in an exemplary mouthpiece.
Figure 7B:
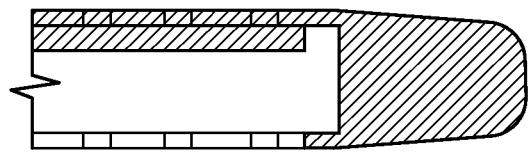
FIG. 7B is a cross-sectional view of the exemplary cheek retractor portion of FIG. 7A.

The cheek retractor portion 130 is illustrated as a hammerhead distal region, which may be attached to the main body portion 110. FIG. 7A is a close-up view of an exemplary cheek retractor portion 130 in an exemplary mouthpiece. FIG. 7B is a cross-sectional view of the exemplary cheek retractor portion 130 of FIG. 7A.

The mouthpiece may be used with a mouth prop 160, as illustrated in FIG. 1 (with a mouth prop 160) and FIG. 2 (illustrated without the mouth prop 160). FIGS. 3A-E provide different close-up views of an exemplary mouth prop 160. The removable strap 310 may be attached to mouth prop 160, which may be used to prop open a patient's mouth and teeth. In this regard, the suction connector portion 120 may additionally have an external plug 220 (FIG. 2C) protruding from the posterior side of the suction connector portion 120. Such a plug 220 may correspond to and serve to connect with an opening in the mouth prop 160. The mouth prop 160 may be reinforced by the presence of the plug 220 in the opening, thereby resulting in a more crush-resistant, nearly incompressible, and stable mouth prop 160. In some embodiments, the suction connector portion 120 may further have a cutout 230 (e.g., which may be shaped as a logo) providing extra interlocking with a corresponding protrusion (e.g., which may also be shaped as a logo) on an external high-suction vacuum adapter.

The mouth prop 160 may be made of thickened silicone material injection molded in a single piece with an elastic strap corresponding to the circumference of the suction connector portion. The mouth prop 160 has an internal, rectangular-shaped female slot designed to fit snugly with the external, rectangular-shaped male plug 220 of the suction connector portion 120 of the mouthpiece. Mouth props may be made in different sizes for differently sized mouths. Because the mouth prop and mouthpiece are detachable from each other, different sizes of each may be mixed and matched as needed for a particular patient's mouth.

The mouthpiece as described herein may be used with a one-piece, autoclavable, high-suction vacuum adapter. Such a high-suction vacuum body adapter may be made of a single homogenous material. Having a single lever design, such a vacuum adapter may function in the same manner as all the current high-suction vacuum evacuators and saliva ejectors in controlling the removal of water, saliva, and debris from the oral cavity to the outside vacuum source. The single lever may be designed to control the removal of water, saliva, and debris from the at least partially enclosed main body through a single, large evacuation conduit within the suction connector portion.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed is:

1. A mouthpiece comprising:
an elastomeric and resilient main body portion having a distal portion and a proximal portion, the main body portion configured as a pocket having an interior defined by:
an anterior wall defined by an exterior edge,
a posterior wall defined by an exterior edge that corresponds to the exterior edge of the anterior wall, and comprising an internal bridge structure, the bridge structure comprising a plurality of protrusions integral with and protruding from an interior surface of the posterior wall and substantially extending a distance between the anterior wall and the posterior wall, wherein the bridge structure is not attached to the anterior wall, wherein the plurality of protrusions of the bridge structure protrude from the interior surface of the posterior wall in a wave shape comprising crests and troughs;
a side wall connecting the exterior edge of the anterior wall to the corresponding exterior edge of the posterior wall; and
a cheek retractor portion connected to the distal portion of the main body portion and wherein the cheek retractor portion extends laterally away from the distal portion of the main body portion.

2. The mouthpiece of claim 1, wherein the plurality of protrusions of the bridge structure comprises a plurality of spaced contact points.

3. The mouthpiece of claim 2, wherein each of the plurality of spaced contact points is at one of the crests of the wave shape.

4. The mouthpiece of claim 2, wherein each of the troughs comprises a space between the contact points.

5. The mouthpiece of claim 1, further comprising a suction connector portion at the proximal portion of the main body, the suction connector portion in fluid communication with the interior of the pocket to a vacuum source, wherein activation of the vacuum source provides suction of fluids from the interior of the pocket toward the vacuum source.

6. The mouthpiece of claim 5, wherein the anterior wall and the posterior wall are bendable, and wherein the bridge structure keeps the anterior wall separated from the posterior wall during suction.

7. The mouthpiece of claim 1, wherein a shape formed by the bridge corresponds to a shape of the anterior wall and/or a shape of the posterior wall.

8. The mouthpiece of claim 1, wherein the anterior wall, the posterior wall, and/or the side wall comprise a plurality of perforations.

9. The mouthpiece of claim 1, wherein the anterior wall further includes a slit along a longitudinal axis of the main body.

10. The mouthpiece of claim 1, further comprising a stability bar protruding from an interior surface of the posterior wall along a longitudinal axis of the main body, the stability bar spaced from the bridge structure.

11. The mouthpiece of claim 1, wherein the main body portion is formed by injection-molding as one piece.

12. The mouthpiece of claim 1, wherein a material that forms the main body portion is a flexible, translucent, high heat-resistant, autoclavable silicone-based material.

13. The mouthpiece of claim 1, wherein the anterior wall and the posterior wall have different thicknesses.

14. The mouthpiece of claim 1, further comprising a detachable mouth prop.

15. The mouthpiece of claim 14, wherein the detachable mouth prop comprises a bite block portion and a strap portion.

16. The mouthpiece of claim 15, wherein the bite block portion and strap portion are injection-molded in one piece.

17. The mouthpiece of claim 16, wherein the strap portion is configured to fit around a suction connector portion at the proximal portion of the main body.

18. The mouthpiece of claim 17, wherein an external surface of the suction connector portion comprises a notch region corresponding to the strap portion, and wherein an external surface of the strap portion is substantially flush with a remaining external surface of the suction connector portion when the strap portion sits in the notch region.

19. The mouthpiece of claim 15, wherein the bite block portion comprises an opening corresponding to a plug connected to the main body.

\* \* \* \* \*